(12) United States Patent
Chapuis (10) Patent No.: US 12,133,817 B2
(45) Date of Patent: Nov. 5, 2024

(54) TREATMENT DEVICE INCLUDING A TOOL-HOLDER AND A TOOL INCLUDING CONTACTLESS ROTATIONAL MOVEMENT MEANS

(71) Applicant: EYE TECH CARE, Rillieux-la-Pape (FR)

(72) Inventor: Philippe Chapuis, Pommiers (FR)

(73) Assignee: EYE TECH CARE, Rillieux-la-Pape (FR)

( * ) Notice: Subject to any disclaimer, the term of this patent is extended or adjusted under 35 U.S.C. 154(b) by 246 days.

(21) Appl. No.: 17/785,462

(22) PCT Filed: Dec. 16, 2020

(86) PCT No.: PCT/EP2020/086440
§ 371 (c)(1),
(2) Date: Jun. 15, 2022

(87) PCT Pub. No.: WO2021/122762
PCT Pub. Date: Jun. 24, 2021

(65) Prior Publication Data
US 2023/0021859 A1    Jan. 26, 2023

(30) Foreign Application Priority Data

Dec. 16, 2019    (FR) ...................................... 1914494

(51) Int. Cl.
*A61F 9/007*    (2006.01)
*A61N 7/02*    (2006.01)
*A61N 7/00*    (2006.01)

(52) U.S. Cl.
CPC ............ *A61F 9/00781* (2013.01); *A61N 7/02* (2013.01); *A61F 9/00745* (2013.01); *A61N 2007/0065* (2013.01); *A61N 2007/0091* (2013.01)

(58) Field of Classification Search
CPC .... A61F 9/00781; A61F 9/00745; A61B 8/10; A61B 8/4411; G01S 7/52082;
(Continued)

(56) References Cited

U.S. PATENT DOCUMENTS 5,162,044 A     11/1992   Gahn et al.
2011/0098601 A1*  4/2011   Huynh ................... H01R 24/58
                                              606/41
(Continued)

FOREIGN PATENT DOCUMENTS

CN    101969899 A       2/2011
CN    102148883 A   *   8/2011
(Continued)

*Primary Examiner* — Sean D Mattson
(74) *Attorney, Agent, or Firm* — BCF LLP (57) ABSTRACT

The present invention relates to a treatment device comprising: —an ultrasound generation unit (3) comprising an ultrasound module (32) including at least a transducer (321), —a hand-held part (2) comprising a gripping body (21), and a head (23) mounted on the body, the hand-held part and the ultrasound generation unit being designed to be joined together by contactless coupling means such that, when the hand-held part and the ultrasound generation unit are joined, the rotational movement of the upstream base between first and second positions causes the rotational movement of the ultrasound module between the first and second positions.

7 Claims, 4 Drawing Sheets

(58) Field of Classification Search
CPC .... A61N 2007/0091; A61N 2007/0065; A61N 2007/0095; A61N 7/02
See application file for complete search history.

(56) References Cited

U.S. PATENT DOCUMENTS

| | | | |
|---|---|---|---|
| 2012/0016239 A1* | 1/2012 | Barthe | A61B 8/4272 600/439 |
| 2013/0111710 A1* | 5/2013 | Hunts | H01F 7/0242 24/303 |
| 2013/0211395 A1* | 8/2013 | Schwartz | A61F 9/00781 606/28 |
| 2016/0175146 A1 | 6/2016 | Gooding et al. | |
| 2016/0175619 A1* | 6/2016 | Lee | A61N 7/022 601/3 |
| 2019/0223837 A1* | 7/2019 | Petrossian | A61B 8/56 |

FOREIGN PATENT DOCUMENTS

| | | |
|---|---|---|
| CN | 102316834 A | 1/2012 |
| CN | 102497839 A | 6/2012 |
| CN | 103093917 A | 5/2013 |
| CN | 104507427 A | 4/2015 |
| CN | 207412301 U | 5/2018 |
| CN | 107427387 A | 1/2021 |
| DE | 4430720 A1 | 6/1995 |
| FR | 3062057 A1 * 7/2018 ......... A61F 9/00781 |
| KR | 2016-0080892 A | 7/2016 |
| KR | 2016-0105952 A | 9/2016 |
| KR | 2019-0036876 A | 4/2019 |
| TW | 200726039 A | 7/2007 |
| WO | 2002/038078 A2 | 5/2002 |
| WO | 2009/103721 A1 | 8/2009 |
| WO | 2016/156381 A1 | 10/2016 |

* cited by examiner

TREATMENT DEVICE INCLUDING A TOOL-HOLDER AND A TOOL INCLUDING CONTACTLESS ROTATIONAL MOVEMENT MEANS

CROSS-REFERENCE TO RELATED APPLICATIONS

This application is a national phase filing under 35 U.S.C. § 371 of International Application No. PCT/EP2020/086440 filed on Dec. 16, 2020, which claims benefit of priority from French Patent Application No. 1914494 filed Dec. 16, 2019, the contents of each of which are hereby incorporated by reference in their entirety.

FIELD OF THE INVENTION

The present invention concerns the general technical field of devices for non-invasive treatment of an ocular pathology via generation of focused or non-focused ultrasound, of high or low intensity.

More particularly, the invention concerns a treatment device including:
a handpiece intended to be operated by a practitioner, and
a unit for generating ultrasound waves for the treatment of an ocular pathology, for example the treatment of glaucoma.

BACKGROUND OF THE INVENTION

Glaucoma is an optical neuropathy i.e. degeneration of the optic nerve, very often leading to an increase in Intraocular Pressure (IOP).

When aqueous humour is no longer evacuated sufficiently rapidly, it accumulates causing an increase in IOP. An increase in IOP compresses the axons in the optic nerve and can also compromise vascularisation of the optic nerve. High IOP over a long period can lead to total loss of vision.

The sole therapeutic approach currently available to treat glaucoma is to reduce intraocular pressure:
either by improving drainage of aqueous humour through the trabecular meshwork and Schlemm's canal of the eye;
or by reducing the production of aqueous humour by the ciliary body of the eye.

A device is known from document WO 2009/103721 to reduce the production of aqueous humour based on the principle of cyclo-coagulation by High Intensity Focused Ultrasound whereby part of the ciliary body is destroyed to reduce the production of aqueous humour.

The device described in WO 2009/103721 allows the treatment of one or more eye regions in one gesture. This device comprises a probe composed of a ring and ultrasound generation means.

The ring has a proximal portion intended to be in contact with a patient's eye, and a distal portion intended to receive the ultrasound generation means.

The ultrasound generation means comprise six transducers having a concave profile of cylinder segment shape, and positioned on a cylindrical ring. Each transducer is adapted to emit high-intensity ultrasound focused on the ciliary body of the eye. This high-intensity focused ultrasound HIFU induces a linear lesion at the ciliary body.

This device therefore allows six linear lesions to be formed at the ciliary boy, each lesion being associated with a respective transducer. These six linear lesions are formed without the need to reposition the device.

The probe described in WO 2009/103721 is a consumable which has to be renewed for each patient.

To reduce the cost of consumables used in the treatment of an ocular pathology, while maintaining the advantages associated with the solution described in WO 2009/103721, the present invention proposes providing ultrasound generation means from two separate parts, only one of these two parts being a consumable, this consumable having a lower manufacturing cost than the ultrasound generation means described in the solution described in WO 2009/103721.

By separating the functions and advantages of the ultrasound generation means according to WO 2009/103721 into two separate parts of which only one is a consumable, it is possible to reduce the costs associated with the treatment of a patient.

With said solution, it is necessary for the practitioner to couple these two parts together for each new treatment of a patient. This coupling must be the simplest possible.

It is therefore one objective of the invention to propose an alternative solution to the device according to WO 2009/103721 wherein the ultrasound generation means are replaced by two separate parts able to be simply coupled together.

SUMMARY OF THE INVENTION

For this purpose, the invention proposes a device for treating an ocular pathology such as glaucoma, the device comprising:
an ultrasound generation unit comprising:
a cradle of axis A-A', the cradle including a downstream base,
an ultrasound module including at least one transducer;
a handpiece comprising:
a gripping body, and
a head mounted on the body, the head including an upstream base, the handpiece and ultrasound generation unit being intended to be associated together so that the outer faces of the upstream and downstream bases extend facing each other, remarkable in that.
the handpiece comprises:
a first contactless coupler housed in the upstream base, and
driving and locking means to move the first coupler in rotation relative to the gripping body, and in that
the ultrasound generation unit comprises:
a second contactless coupler complementing the first coupler and housed in the downstream base of the cradle, the first and second couplers being intended to cooperate together,
so that, when the handpiece and ultrasound generation unit are associated, the rotational movement of the first coupler between first and second positions causes the rotational movement of the ultrasound module between the first and second positions.

The device described above allows an ocular disorder to be treated with equivalent quality to that of the device described in WO 2009/103721, using a handpiece and ultrasound generation unit able to be easily coupled together by the practitioner.

This is made possible via integration:
at the handpiece:
of a first contactless rotating coupler, and
of driving and locking means-such as a motor-allowing rotational movement of the first coupler between a plurality of treatment positions;

at the ultrasound generation unit:
of a single transducer, and
of a second complementing contactless coupler intended to cooperate with the first rotating coupler.

Therefore the technical relationship existing between the handpiece and the ultrasound generation unit—which comprise corresponding technical elements (first coupler and driving means on one hand, transducer and second coupler on the other hand)—allows solving of the technical problem of the present invention, namely the providing of a device for treating an ocular pathology which, with two separate parts able to be simply coupled, allows ultrasound waves to be applied to different regions distributed over the circumference of an eye (without the need to reposition the treatment device).

Preferred but non-limiting aspects of the treatment device of the invention are the following:
the first and second couplers can be of magnetic type;
the first coupler may comprise at least one first magnetic element selected from the group consisting of a permanent magnet and an electromagnet, and the second coupler may comprise at least one second magnetic element selected from the group consisting of a permanent magnet and an electromagnet, the first and second magnetic elements being intended to be positioned facing each other and having opposite polarities;
the first coupler may comprise a plurality of first magnetic elements arranged in the upstream base so that their barycentres extend along a first circle, the first magnetic elements having alternate polarities so that two adjacent first magnetic elements have opposite polarities, the second coupler may comprise a plurality of second magnetic elements arranged in the downstream base so that their barycentres extend along a second circle coaxial to the first circle when the handpiece and ultrasound generation unit are associated, the second magnetic elements having alternate polarities so that two adjacent second magnetic elements have opposite polarities;
the handpiece may comprise at least one electrically conductive trace extending over the outer face of the upstream base and intended to come into contact with at least one connection terminal of the ultrasound generation unit, the electrically conductive trace being circular, the axis of revolution of the electrically conductive trace being coaxial to axis A-A' when the handpiece and ultrasound generation unit are associated;
the radial width of the electrically conductive trace can be greater than or equal to 1 millimetre, preferably greater than or equal to 1.5 millimetres, and more preferably greater than 2 millimetres;
the handpiece may comprise a conduit projecting outwardly from the outer face of the upstream block, and the cradle may comprise a central channel of axis of revolution A-A', the central channel being sized to receive the end of the conduit when the ultrasound generation unit and the handpiece are associated.

The invention also concerns a handpiece of a device for treating an ocular pathology, comprising:
the handpiece, and
an ultrasound generation unit comprising a supporting cradle of axis A-A' including a downstream base, and an ultrasound module including at least one transducer, the handpiece comprising:
a gripping body, and
a head mounted on the body, the head including an upstream base,
the handpiece and ultrasound generation unit being intended to be associated together so that the outer faces of the upstream and downstream bases extend facing each other, noteworthy in that the handpiece comprises:
a first contactless coupler housed in the upstream base, the first coupler being intended to cooperate with a second coupler arranged in the downstream base of the cradle, and
driving and locking means to move the first coupler in rotation relative to the gripping body,
so that, when the handpiece and ultrasound generation unit are associated, the rotational movement of the first coupler between first and second positions causes rotational movement of the ultrasound module between the first and second positions.

The invention also concerns an ultrasound generation unit of a device for treating an ocular pathology, comprising:
the ultrasound generation unit, and
a handpiece comprising:
a gripping body, and
a head mounted on the body, the head including an upstream base,
the ultrasound generation unit comprising:
a supporting cradle of axis A-A', the cradle including a downstream base,
an ultrasound module including at least one transducer, the ultrasound generation unit and the handpiece being intended to be associated together so that the outer faces of the upstream and downstream bases extend facing each other,
noteworthy in that the ultrasound generation unit comprises a second contactless coupler housed in the downstream base of the cradle, the second coupler being intended to cooperate with a first contactless coupler in the upstream base, said handpiece including driving and locking means to move the first coupler relative to the gripping body so that, when the handpiece and ultrasound generation unit are associated, the rotational movement of the first coupler between first and second positions causes rotational movement of the ultrasound module between the first and second positions.

BRIEF DESCRIPTION OF THE DRAWINGS

Other advantages and characteristics of the treatment device of the invention will become better apparent from the following description of several variants of embodiment given as non-limiting examples, in connection with the appended drawings in which.

DETAILED DESCRIPTION OF THE INVENTION

A description is now given of different examples of the treatment device of the invention with reference to the Figures. In these different Figures, equivalent elements are designated by the same reference numeral.

1. General

Figure 1:
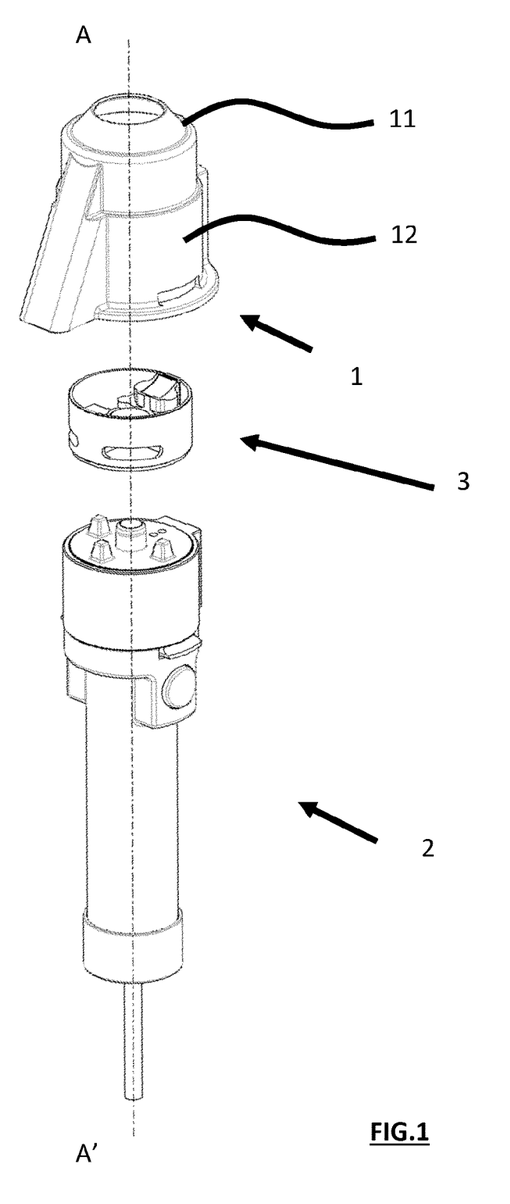
FIG. 1 schematically illustrates an exploded perspective view of a device for treating an ocular pathology.

With reference to FIG. 1, the treatment device comprises:
a ring 1,
a handpiece 2, and
an ultrasound generation unit 3.

The ring 1, the handpiece 2 and the ultrasound generation unit 3 are intended to be assembled together and to extend along an axis A-A' to form the treatment device.

The ring 1 and the ultrasound generation unit 3 are consumables of the treatment device, while the handpiece 2 is intended to be reused for the treatment of a plurality of patients.

It is thus possible to integrate the costliest components of the device in the handpiece and thereby reduce the cost of the consumables used in the treatment of an ocular pathology.

2. Treatment Device

2.1. Ring

The ring 1 allows adequate and constant positioning of the assembly composed of the handpiece 2 and the ultrasound generation unit 3, both for centring and in respect of the distance between the sclera and the means of the ultrasound generation unit 3.

The ring 1 comprises a conical frustum 11 of axis A-A', and a peripheral skirt 12 coaxial to the conical frustum 11.

The conical frustum 11 is open at its two ends. The small base of the conical frustum 11 is intended to come into contact with the eye of a patient.

The skirt 12 comprises a cylindrical wall extending outwardly from the large base of the conical frustum 11. This skirt 12 forms a housing intended to receive the ultrasound generation unit 3.

The ring 1 is adapted to be filled with a coupling fluid to allow transmission of treating acoustic waves towards the patient's eye.

Such a ring being known to persons skilled in the art, in particular from document WO 2016/156381, it will not be described in further detail in the remainder hereof.

2.2. Handpiece

Figure 2:
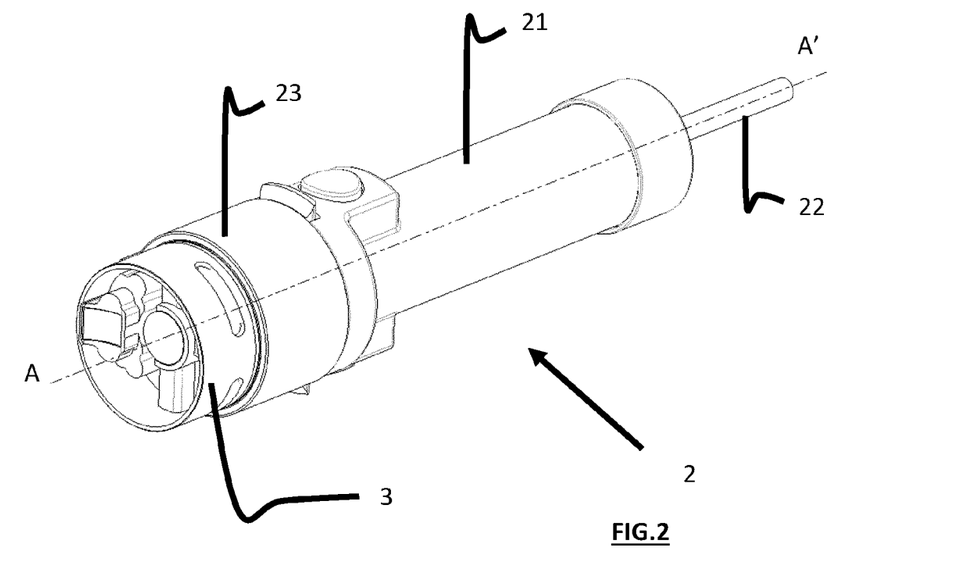
FIG. 2 schematically illustrates a perspective view of a handpiece and ultrasound generation unit assembled together.

As illustrated in FIG. 2, the handpiece 2 is intended to be associated with the ultrasound generation unit 3. As will become apparent from the following description, the handpiece 2 particularly allows rotational movement of the ultrasound generation unit 3 over a plurality of treatment positions.

2.2.1. Gripping Body

Figure 3:
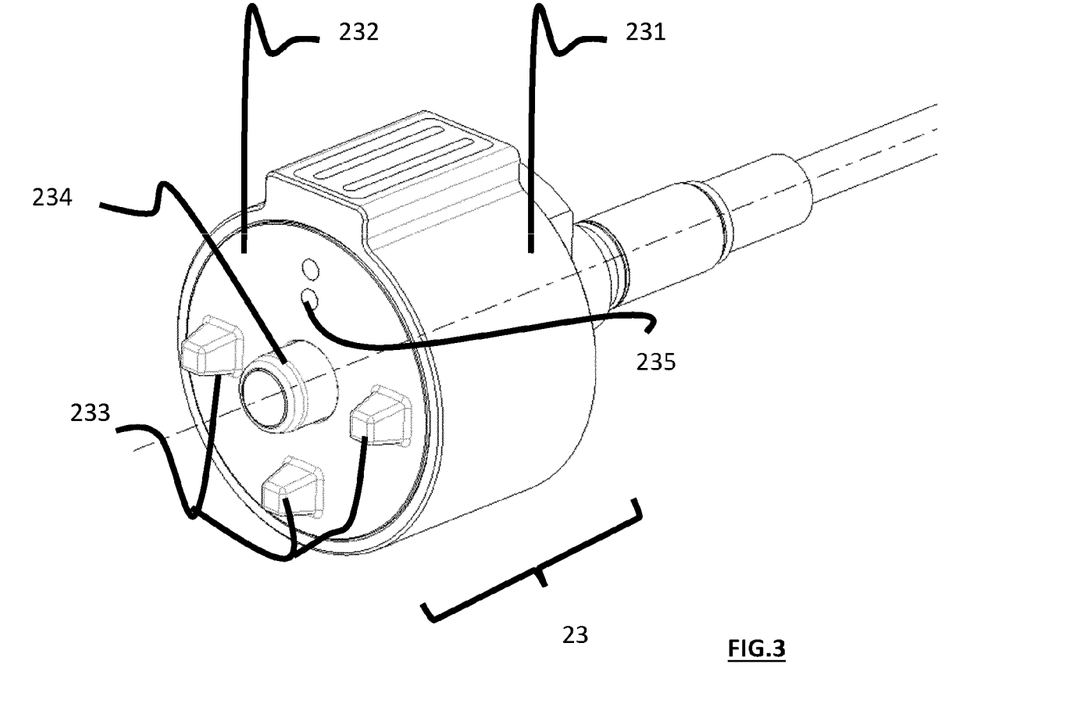
FIG. 3 is a perspective view of a portion of the handpiece.

With reference to FIGS. 2 and 3, the handpiece 2 comprises a gripping body 21 enabling the practitioner to manipulate the device.

The gripping body 21 extends longitudinally along axis A-A'. It comprises an actuation button for activating the ultrasound generation unit 3 to produce treating ultrasound waves.

2.2.2. Connecting Lead

The handpiece 2 also comprises an electrical lead 22 connecting with one of the ends of the gripping body 21.

The electrical connecting lead 22 particularly allows:
transmission of data (control signals, optionally measurement signals, etc.) between a remote-control unit (not illustrated) and the ultrasound generation unit 3; and
powering of the ultrasound generation unit 3 with electrical power to produce treating ultrasound waves.

2.2.3. Head

The handpiece also comprises a head 23 at the other end of the gripping body 21. The ultrasound generation unit 3 is intended to be coupled to the handpiece 2 at the head 23.

The head 23 is composed of a cylindrical casing 231 and an upstream base 232 of which the outer face is intended to come to lie facing a downstream base of the ultrasound generation unit 3.

The head 23 comprises driving and locking means—such as a motor—to cause rotational movement of the upstream base 232 relative to the gripping body 21. These driving and locking means are arranged in the cylindrical casing 231.

The head 23 also comprises one (or more) lug(s) 233 projecting outwardly from the upstream base 232. Each lug 233 is intended to cooperate with a respective imprint arranged in the downstream base of the ultrasound generation unit 3.

The head 23 may also comprise magnetic coupling means—such as one (or more) permanent magnet(s)—arranged in the upstream base 232. These magnetic coupling means are intended to cooperate:
either directly with a cradle of the ultrasound generation unit 3 when the cradle is in magnetic material—such as magnetic stainless steel or magnetically charged plastic;
or with complementing coupling means—such as one (or more) permanent magnet(s)—arranged in the downstream base of the ultrasound generation unit 3.

These magnetic coupling means allow removable attaching of the ultrasound generation unit 3 onto the handpiece 2. This provides facilitated handling of the device by the practitioner.

The head 23 may additionally comprise a camera mounted in a conduit 234 projecting outwardly from the upstream base 232. The camera allows acquisition of images of the eye to be treated, in particular to verify proper centring of the treatment device on the patient's eye.

The head 23 also comprises one (or more) electrically conductive trace(s) 235 extending over the outer face of the upstream base 232. Each trace 235 is intended to come into contact with a connection terminal of the ultrasound generation unit 3 to allow electrical connection of the ultrasound generation unit with the handpiece.

Advantageously, the size of each trace can be adapted to take into account a change in the position of the connection terminal associated therewith.

The position of each connection terminal can effectively vary from one ultrasound generation unit to another, in particular as a function of the eye dimensions of the patient to be treated. Therefore, at least one of the dimensions of each electrically conductive trace can be designed to be greater than or equal to 1 millimetre, preferably greater than or equal to 1.5 millimetres, more preferably greater than 2 millimetres to take into account variations in the positioning of the connection terminals.

2.3. Ultrasound Generation Unit

The ultrasound generation unit 3 allows generation of ultrasound energy. It comprises a supporting cradle 31, an ultrasound module 32 including a transducer 321 and a seal 33.

Advantageously, the cradle 31 and the ultrasound module 32 are manufactured independently then assembled to form the ultrasound generation unit 3. This allows the manufacture of ultrasound modules 32 in series which reduces manufacturing costs of the ultrasound generation unit 3.

2.3.1. Cradle

The cradle 31 is composed of an annular ring of axis A-A'. The cradle 31 comprises:
- a downstream base 311 on the inner face of which the ultrasound module 32 is attached (e.g. using fixing screws);
- an outer side wall 317, and
- an inner side wall defining a central channel 315 passing through the downstream base 311.

Figure 6:
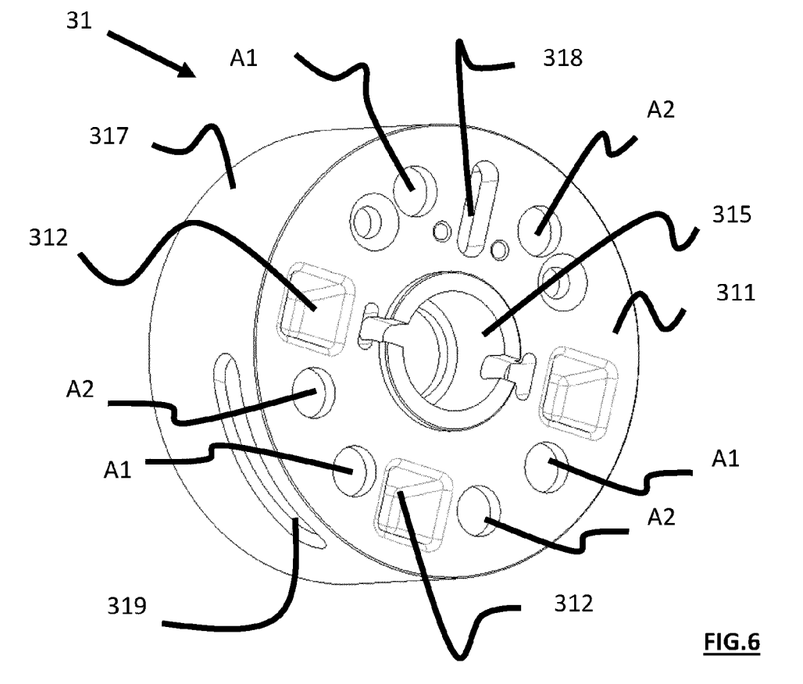

The downstream base 311, on its outer face, may comprise magnetic coupling means complementing the coupling means provided in the head of the handpiece. In the embodiment illustrated FIG. 6, the coupling means comprise a plurality of permanent magnets A1, A2 arranged in the downstream base 311 so that their barycentres extend along a circle of which the centre belongs to axis A-A'. Advantageously, these permanent magnets can be arranged to have alternate polarities so that two adjacent permanent magnets A1, A2 have opposite polarities. They are intended to cooperate with a plurality of permanent magnets arranged in the upstream base 232 of the handpiece 2, each permanent magnet of the upstream base 232 being intended to come to lie facing a corresponding magnet of the downstream base 311.

The outer side wall 317 of the cradle 31 may also comprise through holes 319 (e.g. oblong) to facilitate evacuation of air bubbles when the ring 1 is filled with the coupling fluid.

The central cylindrical channel 315 has a larger diameter than the diameter of the conduit 234. It is intended to receive the end of the conduit 234 when the ultrasound generation unit 3 and the handpiece 2 are coupled together. Therefore, when the handpiece 2 and the ultrasound generation unit 3 are associated, the central channel 315 and the conduit 234 are coaxial. In addition to their function of housing an image-taking camera, the central channel 315 and the conduit 234 form guide means facilitating alignment of the handpiece 2 and ultrasound generation unit 3.

The end of the central channel 315 opposite the outer face of the downstream base 311 comprises the plate 316 transparent to light radiation. This transparent plate 316 can be, for example, a circular disc bulging outwardly from the central channel 315, such as a convergent lens. This allows evacuation of any bubbles (contained in the coupling fluid) out of the field of the camera contained in the handpiece 2.

The cradle 31 also comprises one (or more) imprints 312 opening onto the outer face of the downstream base 311. As previously indicated, each imprint 312 is adapted to receive a respective lug 233. Cooperation between the lugs 233 and imprints 312 allows the ultrasound generation unit 3 to be driven in rotation when the upstream base 232 of the handpiece 2 moves in rotation. Advantageously, each imprint is a non-through hole. In other words, each imprint comprises a bottom 313. This prevents coupling fluid contained in the ring from coming into contact with the handpiece 2 by circulating through the imprint (or imprints).

Figure 5:
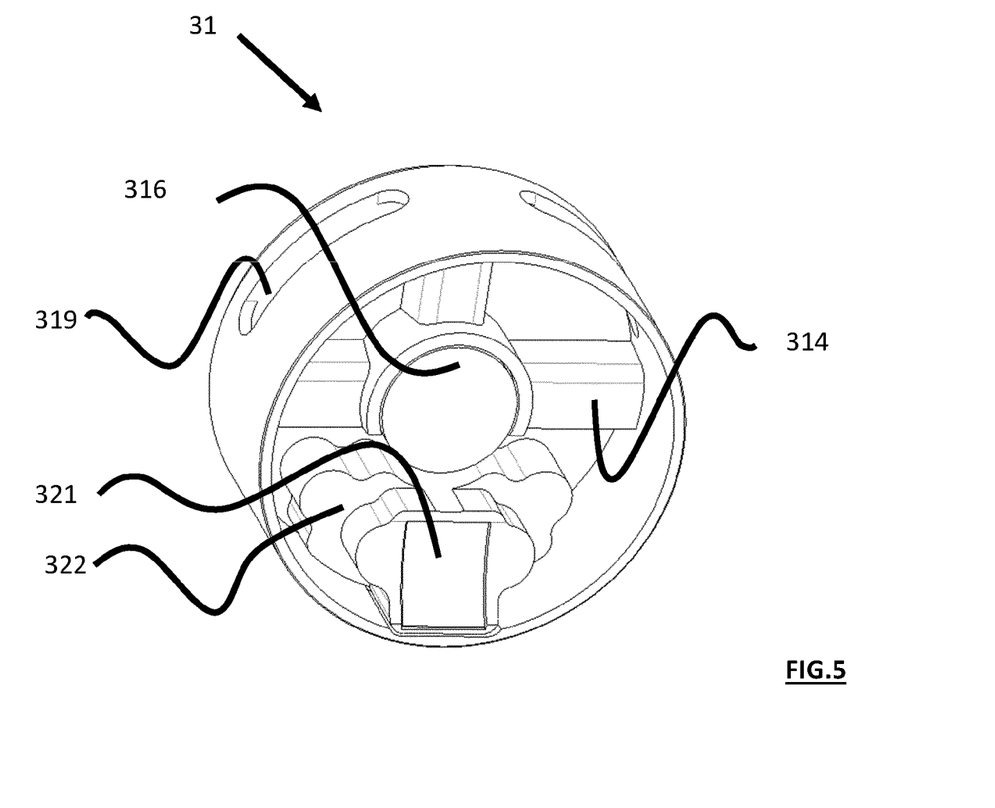

As illustrated FIG. 5, the cradle 31 also comprises one (or more) radial cross-member(s) 314 extending radially over the inner face of the downstream base 311. This (or these) cross-member(s) allow(s) the rigidity of the cradle to be increased. It is thereby possible to reduce the thickness of the constituent walls of the cradle 31 to limit the weight of the ultrasound generation unit 3.

Advantageously, the downstream base 311 comprises a through radial slit 318 extending radially between the centre and periphery of the downstream base 311. This radial slit 318 allows passing of the connection terminal(s) 323 of the ultrasound module 32 attached to the inner face of the cradle 31, so that this (or these) connection terminals 323 project outwardly from the outer face of the downstream base 311. Since the through opening arranged in the downstream base 311 consists of a radial slit, this makes it possible—without requiring modification of the cradle 31—to vary the position of the ultrasound module 32 in the cradle 31 to take into account variations in the dimensions of the eyes to be treated. Therefore, from a cradle 31 and an ultrasound module 32 of standard dimensions, it is possible to obtain different (particularly three) models of ultrasound generation unit 3, each model being adapted to treat an eye of respective size. This allows a reduction in the manufacturing costs of the ultrasound unit 3.

2.3.2. Ultrasound Module

The ultrasound module 32 allows the production of acoustic waves for treating an ocular pathology.

The ultrasound module 32 comprises a transducer 321, a casing 322 and one (or more) connection terminals 323.

The transducer 321 generates treating acoustic waves in a direction opposite to the downstream base 311. The transducer 321 includes a radiating element for generating acoustic waves. The profile of the radiating element can be adapted to allow orienting and focusing of ultrasounds at a given point. As a variant, the transducer 321 may comprise one (or more) reflectors to reflect, orient and focus at a given point the acoustic waves produced by the radiating element.

The casing 322 forms a support for the transducer 321. It contains an electronic circuit board for driving the transducer 321. This electronic board can comprise a memory in which powering parameters of the transducer 321 are stored. The casing is adapted to be attached onto the downstream base 311. It also contains the connection terminal(s) 323.

Figure 4:
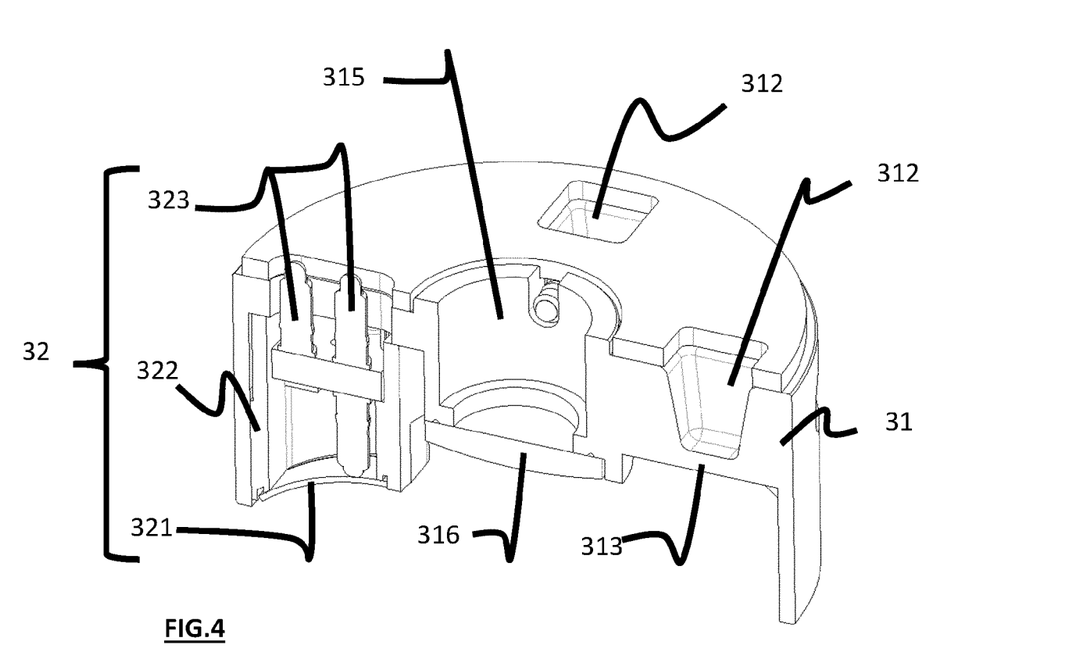
FIGS. 4 to 7 schematically illustrate different perspective views of the ultrasound generation unit.

The connection terminal(s) 323 are intended to come into contact with the electrically conductive trace(s) 235 to connect the handpiece 2 electrically to the ultrasound generation unit 3. In the embodiment illustrated FIG. 4, the ultrasound module 32 comprises two connection terminals 323, one being dedicated to passing of current for electric powering and the other being dedicated to the passing of control and measurement electrical signals. Each connection terminal may comprise a spring electrical connector. This allows consideration to be given to different mechanical tolerances related to assembling of the ultrasound module 32 onto the cradle 31.

2.3.3. Seal

The seal 33 prevents coupling fluid contained in the ring 1 from coming into contact with the connection terminal(s) 323 and electrically conductive trace(s). For this purpose, the seal is intended to extend around the connection terminals 323.

Figure 7:
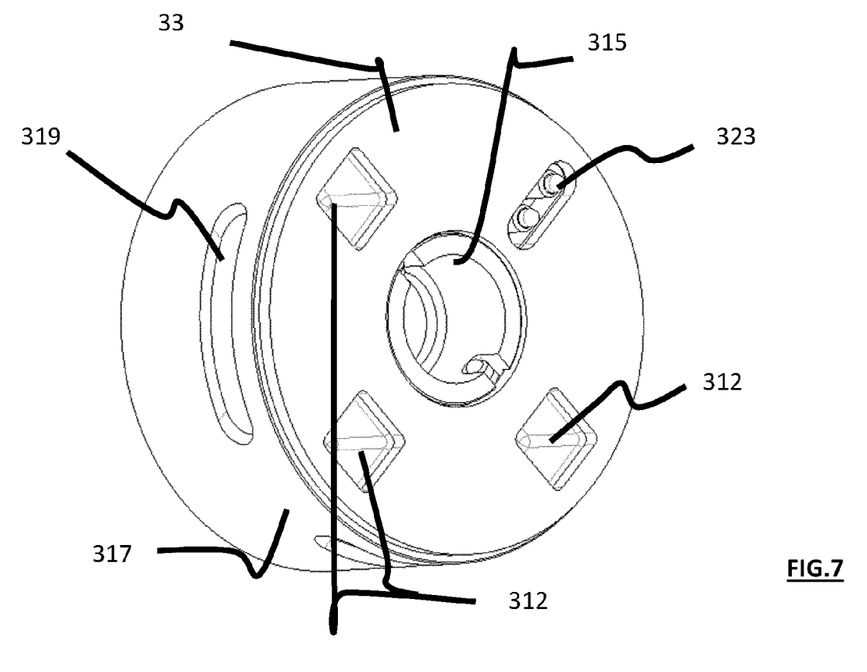

In the embodiment illustrated FIG. 7, the seal is disc-shaped and extends over the entire outer face of the downstream base 311. This (in addition to ensuring sealing of the device at the connection terminals 323) prevents coupling fluid from coming into contact with the handpiece 2. It allows improved stability of the device along axis A-A'.

3. Operating Principle

A description is now given of an example of procedure for use of the device described above to treat the eye of a patient lying on an operating table.

In one step, the practitioner couples the handpiece 2 to the ultrasound generation unit 3. The practitioner brings the upstream base 232 close to the downstream base 311 and engages the conduit 234 into the central channel 315, the magnetic coupling means tending to facilitate the centring (of the handpiece 2 relative to the ultrasound generation unit 3) by means of the magnetic fields which they generate. The connection terminal(s) 323 come into contact with the electrically conductive trace(s) 235 and the coupling means ensure removable attachment of the ultrasound generation unit 3 to the handpiece 2.

The practitioner next inserts the assembly composed of the handpiece 2 and ultrasound generation unit 3 onto the ring 1. Once the device is assembled, the practitioner places the device on the patient's eye and fills the ring 1 with the coupling fluid.

When the device is in proper position and the transducer 321 is immersed in the coupling fluid, the practitioner initiates treatment of the patient by pressing on the actuation button of the handpiece 2.

The ultrasound generation unit 3 produces treating acoustic waves towards a first zone of the patient's eye for a predefined treatment period. Once this predefined period has elapsed, the driving and locking means are actuated. They drive the upstream base 232 in rotation. The force applied by the lugs 233 on the downstream base 311 at the imprints 312 causes rotational movement of the ultrasound generation unit 3.

Once the transducer 321 is positioned at a second treatment position, the driving and locking means are de-actuated: the ultrasound generation unit 3 is immobilised and actuated to produce treating acoustic waves towards a second zone of the eye for the predefined period.

The steps of treatment and movement are repeated to treat different zones over the entire circumference of the patient's eye.

Therefore, the above-described device—at lower manufacturing cost than that of the device described in WO 2009/103721—allows the treatment of several zones distributed over the entire circumference of an eye, without necessitating action by the practitioner to reposition the treatment device between each emission of ultrasound.

4. Variant of Embodiment

A variant of embodiment is now described developed by the Applicant. The reader will appreciate that solely elements differing between the above-described device and the variant of embodiment below will be described in the remainder hereof.

To facilitate assembly of the device, and in particular association of the handpiece 2 with the ultrasound generation unit 3, the inventors propose to overcome the lugs 233 and imprints 312 provided in the upstream and downstream bases 232, 311.

More specifically, in a second variant of embodiment of the invention:
 the handpiece 2 comprises a first contactless coupler housed in the upstream base 232; and
 the ultrasound generation unit 3 comprises a second contactless coupler housed in the downstream base 311 of the cradle 31, the second coupler complementing the first coupler.

The first and second couplers are therefore intended to cooperate together and play the part of the lug(s) and imprint(s) 233, 312 so that the rotational movement of the upstream base 232 between two treatment positions causes rotational movement of the ultrasound module 32 between the first and second positions.

The first and second contactless couplers can each consist of one (or more) permanent magnets or electromagnets of opposite (North/South) polarity.

Replacement of the lugs and imprints by contactless couplers overcomes the restriction in respect of angle orientation of the handpiece 2 relative to the ultrasound generation unit 3 when these are coupled together. The sole restriction to be met to allow coupling of the handpiece 2 and ultrasound generation unit 3 then concerns alignment along axis A-A' between the central channel 315 and the conduit 234 (to be fitted into the central channel). This facilitates association by the practitioner of the handpiece 2 with the ultrasound generation unit 3.

The reader will appreciate that the first and second couplers can be means of magnetic type additional to the coupling means previously described, or they can be the coupling means.

Advantageously, the shape of the electrically conductive trace(s) can be adapted to ensure contact between the connection terminal(s) and the trace(s) irrespective of the angular orientation of the handpiece 2 relative to the ultrasound generation unit 3. In particular, provision can be made for each electrically conductive trace to be circular and positioned on the upstream base so that the axis of revolution of the trace is coaxial to axis A-A' when the handpiece 2 and ultrasound generation unit 3 are associated.

Therefore, the technical elements of this variant of embodiment allow facilitated coupling by the practitioner of the handpiece 2 and ultrasound generation unit 3, to obtain a treatment device adapted to apply ultrasound waves to different zones distributed over the entire circumference of the eye (without necessitating repositioning of the treatment device).

The reader will have understood that numerous modifications can made to the previously described invention without physically departing from the novel teaching and advantages described herein.

The invention claimed is:

1. A device for treating an ocular pathology, the device comprising:
 an ultrasound generation unit comprising:
  a cradle of axis A-A', the cradle including a downstream base, and
  an ultrasound module including at least one transducer; and
 a handpiece comprising:
  a gripping body, and
  a head mounted on the body, the head including an upstream base,
 the handpiece and the ultrasound generation unit being intended to be associated together so that outer faces of the upstream and downstream bases extend facing each other,
 wherein:
 the handpiece comprises:
  a first contactless coupler housed in the upstream base, wherein the first contactless coupler comprises a plurality of first magnetic elements arranged in the upstream base so that their barycentres extend along a first circle, the first magnetic elements having alternate polarities so that two adjacent first magnetic elements have opposite polarities, and
  driving and locking means to move the first contactless coupler in rotation relative to the gripping body, and
 the ultrasound generation unit comprises:
  a second contactless coupler complementing the first contactless coupler and housed in the downstream base of the cradle, the first and second contactless couplers being intended to cooperate together, wherein the second contactless coupler comprises a plurality of second magnetic elements arranged in the downstream base so that their barycentres extend along a second circle, centers of the first and second circles being coaxial with one another when the handpiece and the ultrasound generation unit are associated, the second magnetic elements having alternate polarities so that two adjacent second magnetic elements have opposite polarities so that, when the handpiece and the ultrasound generation unit are associated, the rotational movement of the first contactless coupler between first and second positions causes rotational movement of the ultrasound module between the first and second positions.

2. The treatment device according to claim 1, wherein:
the first contactless coupler comprises at least one first magnetic element selected from the group consisting of a permanent magnet and an electromagnet, and
the second contactless coupler comprises at least one second magnetic element selected from the group consisting of a permanent magnet and an electromagnet,
the first and second magnetic elements being intended to be positioned facing each other and having opposite polarities.

3. The treatment device according to claim 1, wherein the handpiece comprises at least one electrically conductive trace extending on the outer face of the upstream base and intended to come into contact with at least one connection terminal of the ultrasound generation unit, the electrically conductive trace being circular, an axis of revolution of the electrically conductive trace being coaxial to the axis A-A' when the handpiece and the ultrasound generation unit are associated.

4. The treatment device according to claim 3, wherein the radial width of the electrically conductive trace is greater than or equal to 1 millimetre.

5. The treatment device according to claim 4, wherein the radial width of the electrically conductive trace is greater than or equal to 1.5 millimetres.

6. The treatment device according to claim 5, wherein the radial width of the electrically conductive trace is greater than 2 millimetres.

7. The treatment device according to claim 1, wherein:
the handpiece comprises a conduit projecting outwardly from the outer face of the upstream base, and wherein:
the cradle of the ultrasound unit comprises a central channel extending along the axis A-A',
the central channel being sized to receive an end of the conduit when the ultrasound generation unit and the handpiece are associated.

* * * * *